United States Patent
Visuri et al.

(10) Patent No.: US 6,428,531 B1
(45) Date of Patent: Aug. 6, 2002

(54) PHOTOACOUSTIC REMOVAL OF OCCLUSIONS FROM BLOOD VESSELS

(75) Inventors: Steven R. Visuri, Livermore; Luiz B. Da Silva, Danville; Peter M. Celliers, Berkeley; Richard A. London, Orinda; Duncan J. Maitland, IV, Lafayette; Victor C. Esch, San Francisco, all of CA (US)

(73) Assignees: The Regents of the University of California, Oakland; Endovasix, Inc., Belmont, both of CA (US)

( * ) Notice: Subject to any disclaimer, the term of this patent is extended or adjusted under 35 U.S.C. 154(b) by 0 days.

(21) Appl. No.: 09/604,454

(22) Filed: Jun. 27, 2000

Related U.S. Application Data

(63) Continuation of application No. 08/955,858, filed on Oct. 21, 1997, now abandoned.

(51) Int. Cl.[7] .............................................. A61B 18/18
(52) U.S. Cl. ............................ 606/7; 606/15; 606/22; 607/89; 128/898
(58) Field of Search ............................ 606/2, 3, 7, 10, 606/11, 13–17; 607/89, 93; 604/20, 21

(56) References Cited

U.S. PATENT DOCUMENTS

| | | | |
|---|---|---|---|
| 5,041,108 A | * 8/1991 | Fox et al. ..................... 606/7 |
| 5,109,859 A | * 5/1992 | Jenkins .................. 128/662.03 |
| 5,116,227 A | * 5/1992 | Levy .......................... 433/216 |
| 5,192,278 A | * 3/1993 | Hayes et al. ................. 606/15 |
| 5,224,942 A | 7/1993 | Beuchat et al. |
| 5,350,375 A | * 9/1994 | Deckelbaum et al. .......... 606/7 |
| 6,022,309 A | 2/2000 | Celliers et al. |
| 6,080,148 A | 6/2000 | Damasco et al. |
| 6,106,546 A | 8/2000 | Gregory |
| 6,139,543 A | * 10/2000 | Esch et al. ..................... 606/7 |
| 6,210,400 B1 | * 4/2001 | Hebert et al. .................. 606/7 |

FOREIGN PATENT DOCUMENTS

WO     WO9916366     4/1999

OTHER PUBLICATIONS

Wolbarsht, "Interactions Between Material Processing and Surgery", 5 pps., Dept. of Ophthalmology, Duke University, Durham, NC.

* cited by examiner

*Primary Examiner*—Linda C. M. Dvorak
*Assistant Examiner*—A. Farah
(74) *Attorney, Agent, or Firm*—Skjerven Morrill MacPherson LLP; K. Alison de Runtz

(57) ABSTRACT

Partial or total occlusions of fluid passages within the human body are removed by positioning an array of optical fibers in the passage and directing treatment radiation pulses along the fibers, one at a time, to generate a shock wave and hydrodynamics flows that strike and emulsify the occlusions. A preferred application is the removal of blood clots (thrombin and embolic) from small cerebral vessels to reverse the effects of an ischemic stroke. The operating parameters and techniques are chosen to minimize the amount of heating of the fragile cerebral vessel walls occurring during this photo acoustic treatment. One such technique is the optical monitoring of the existence of hydrodynamics flow generating vapor bubbles when they are expected to occur and stopping the heat generating pulses propagated along an optical fiber that is not generating such bubbles.

20 Claims, 11 Drawing Sheets

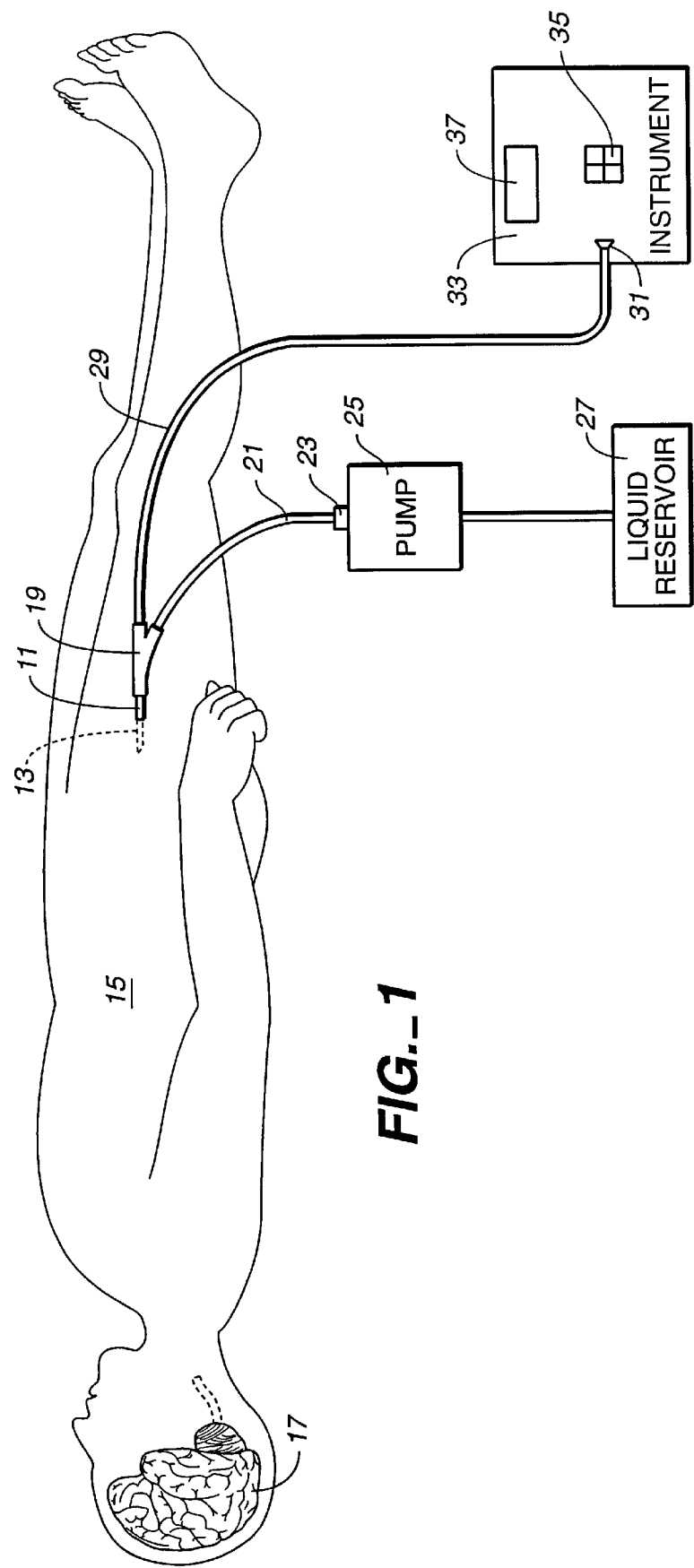
FIG._1

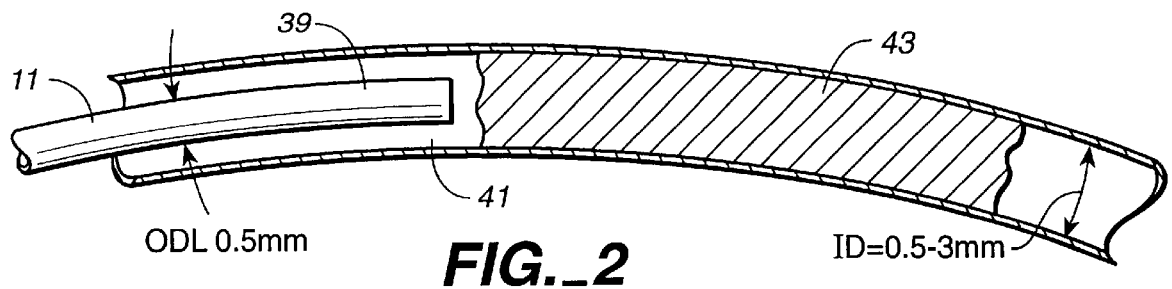
FIG._2
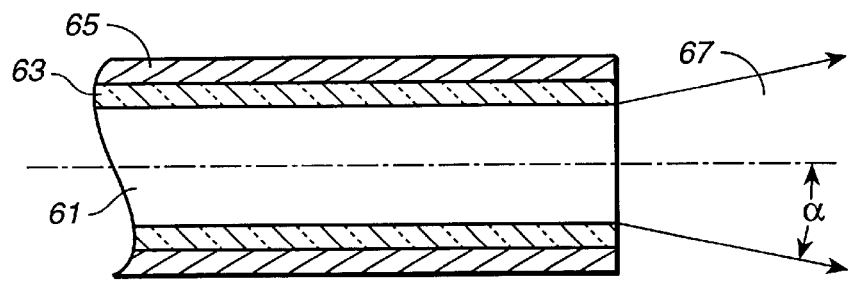
FIG._4
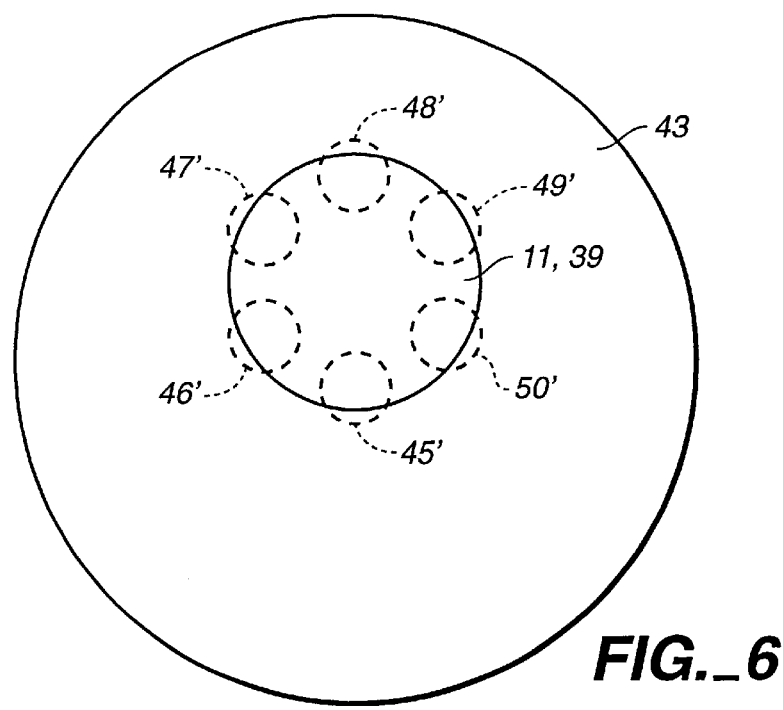
FIG._6

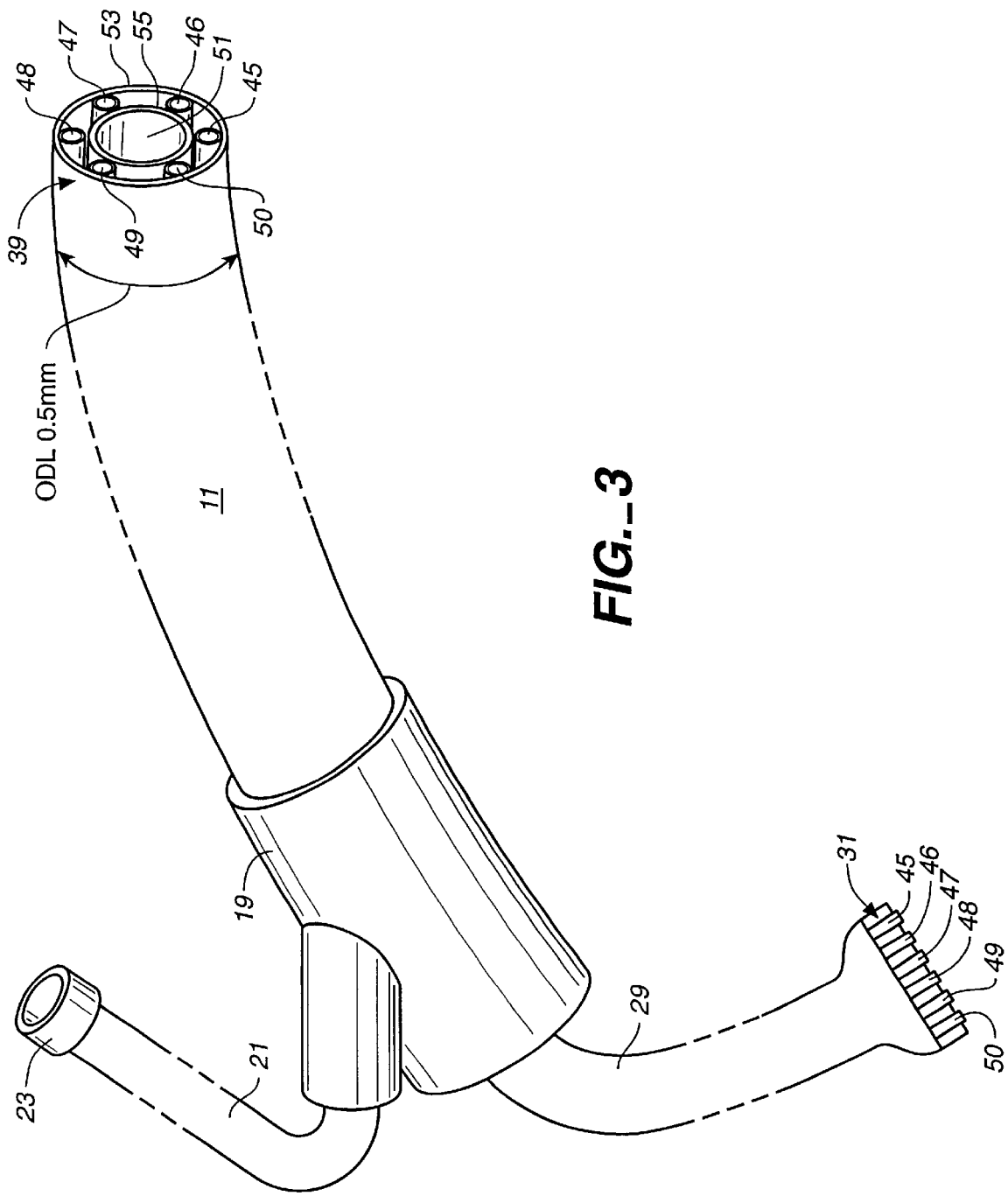
FIG._3

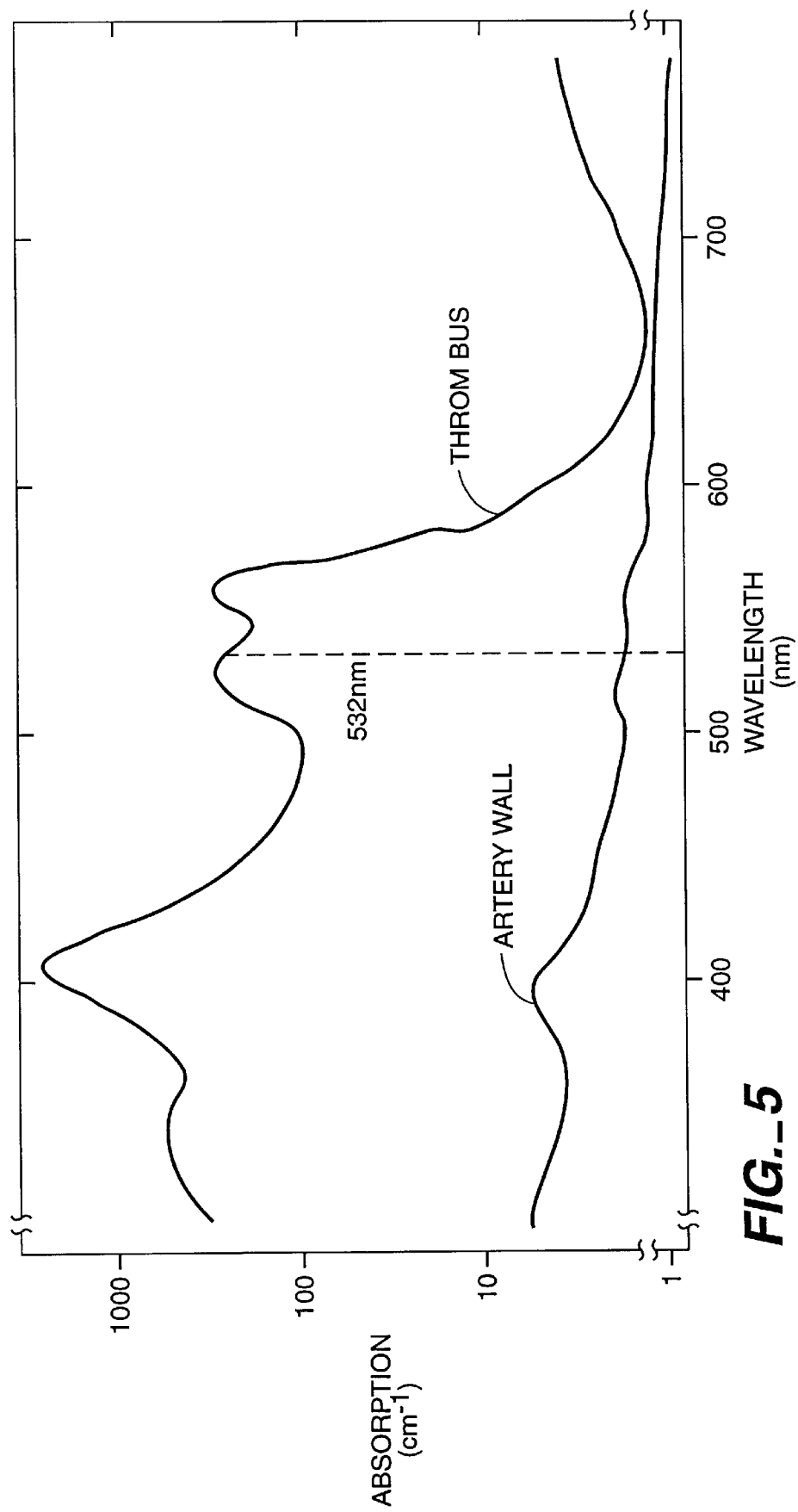
FIG._5

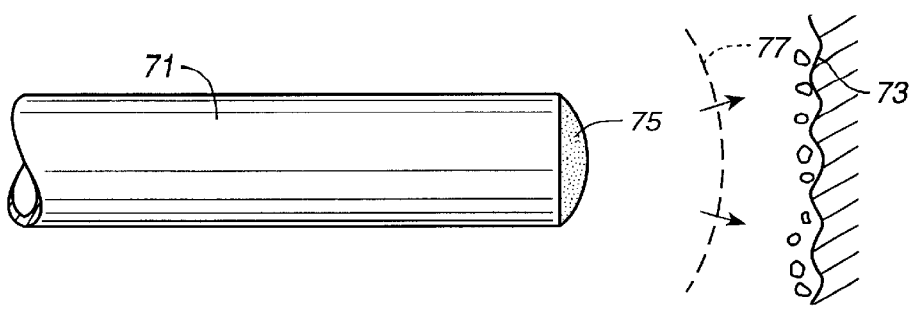
FIG._7A
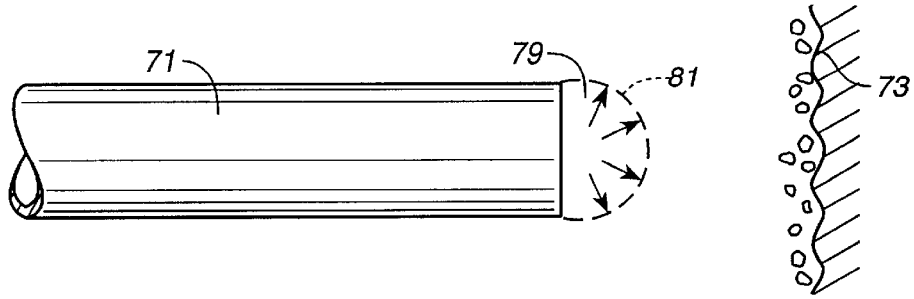
FIG._7B
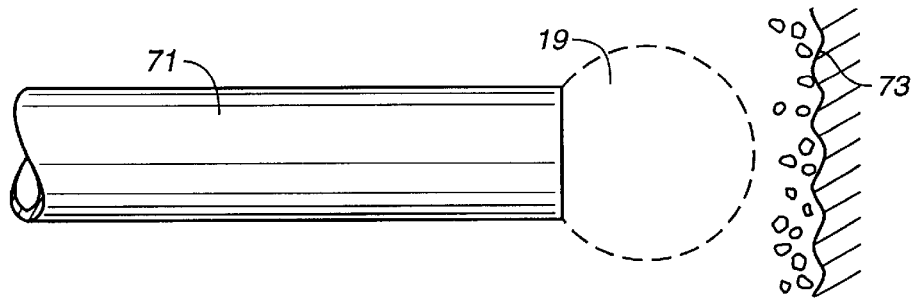
FIG._7C
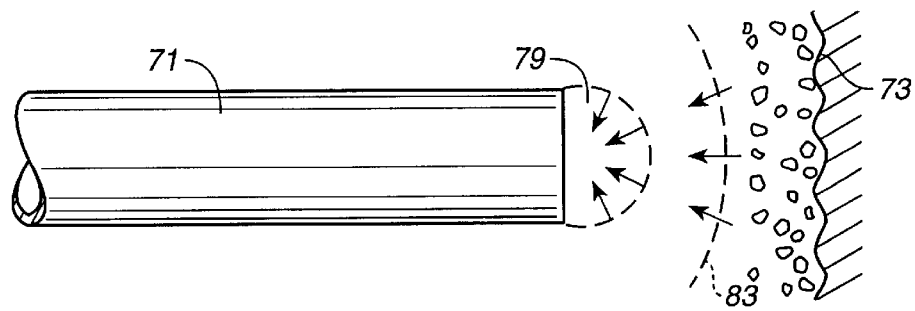
FIG._7D
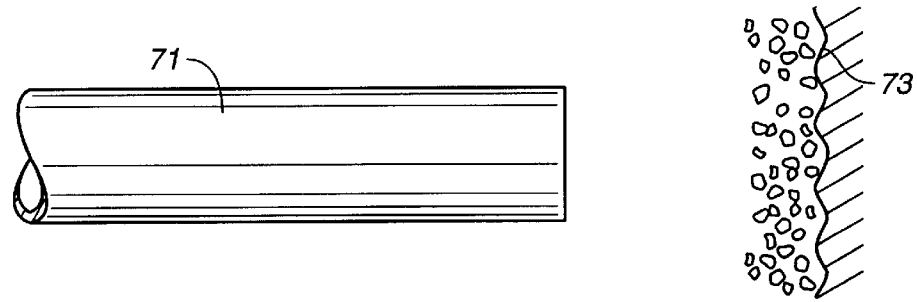
FIG._7E

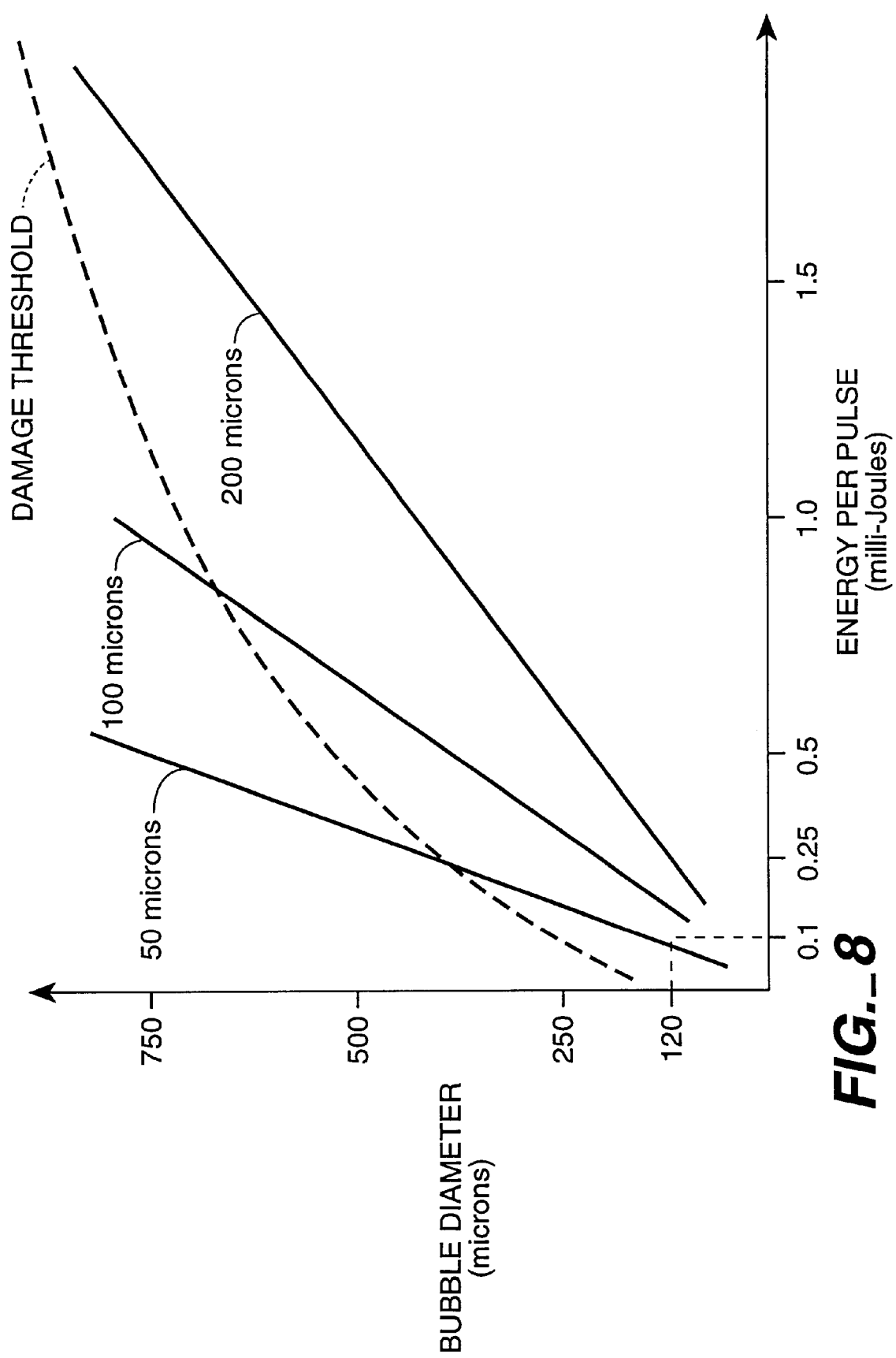
FIG._8

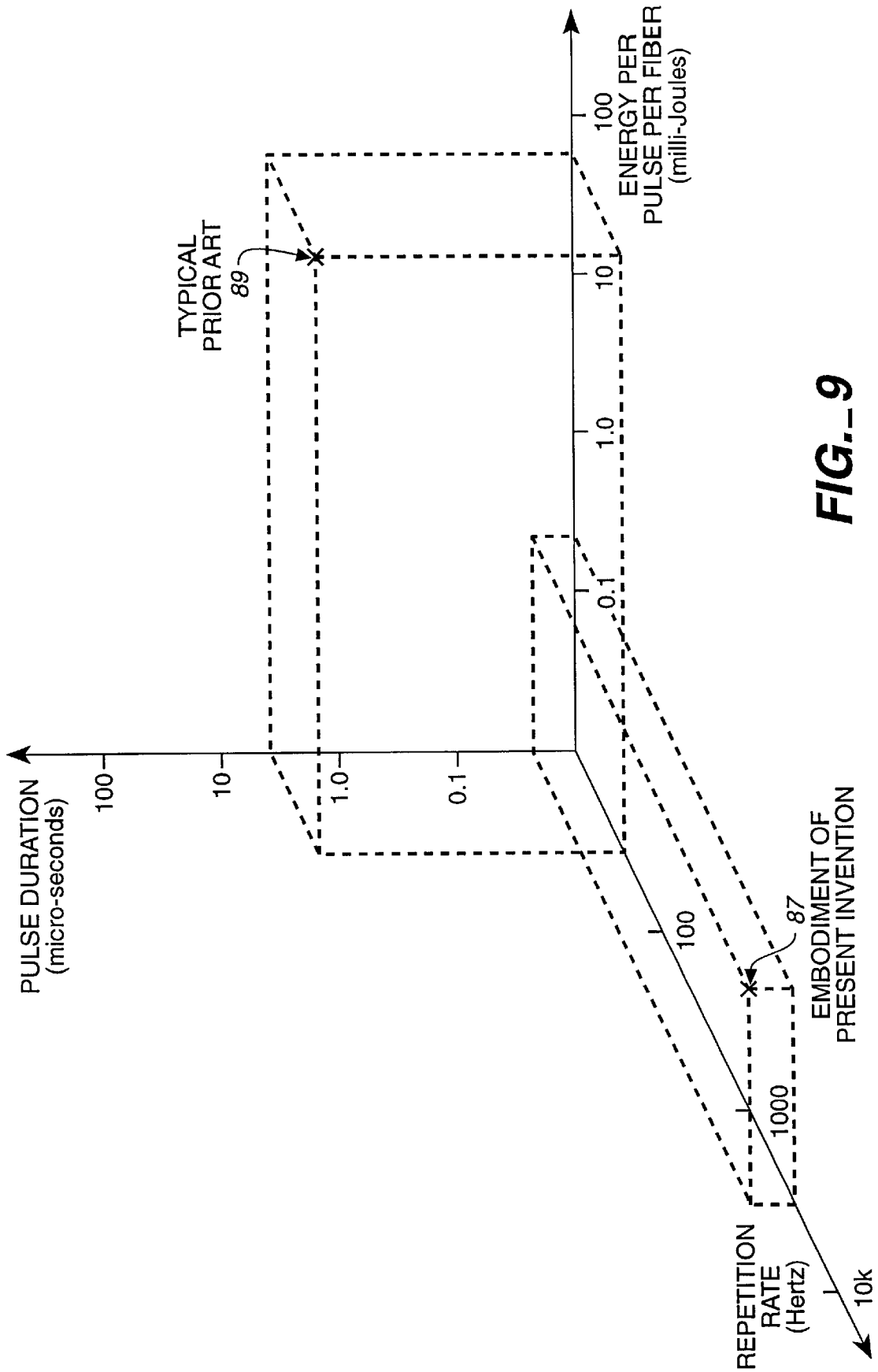
FIG._9

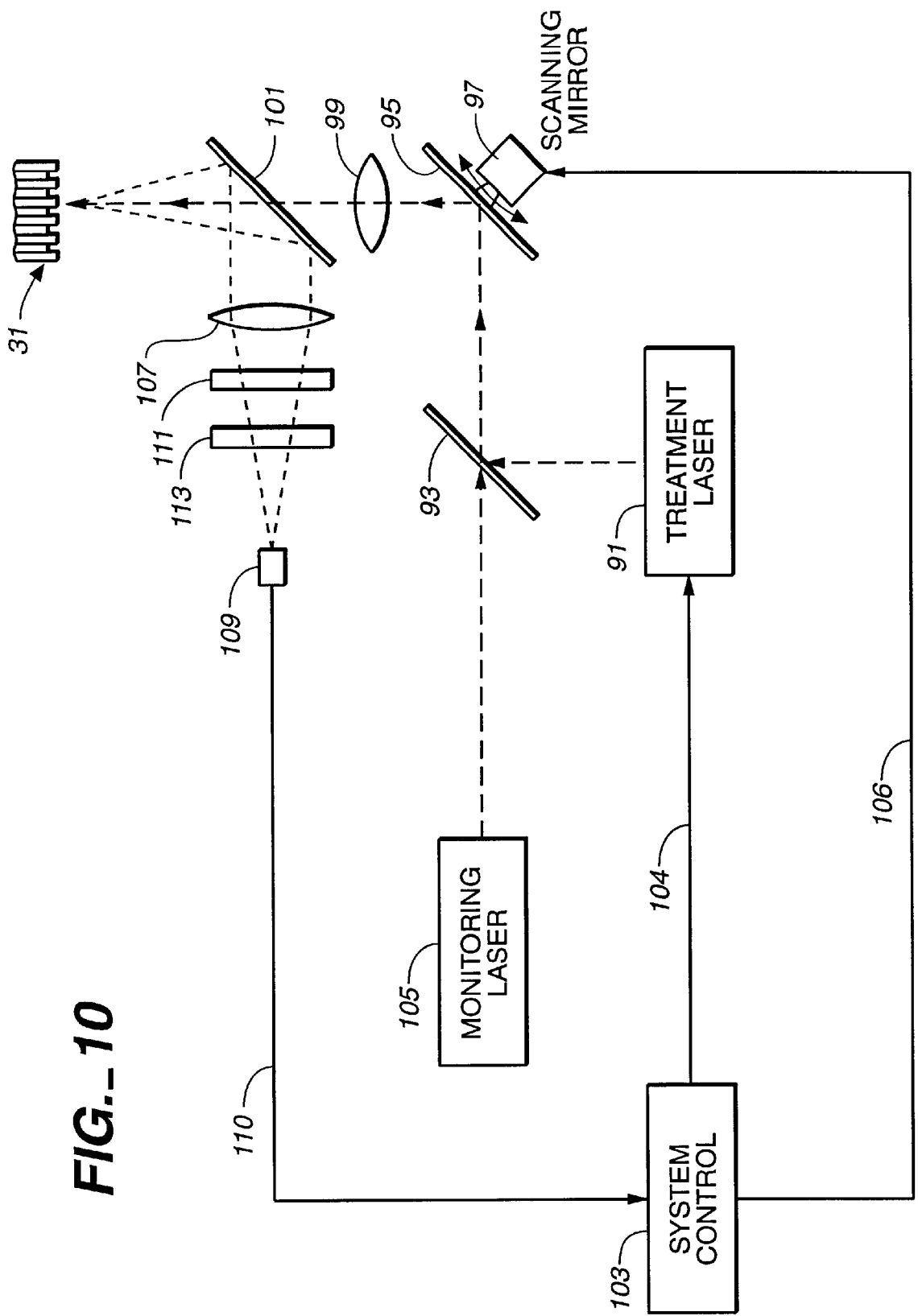

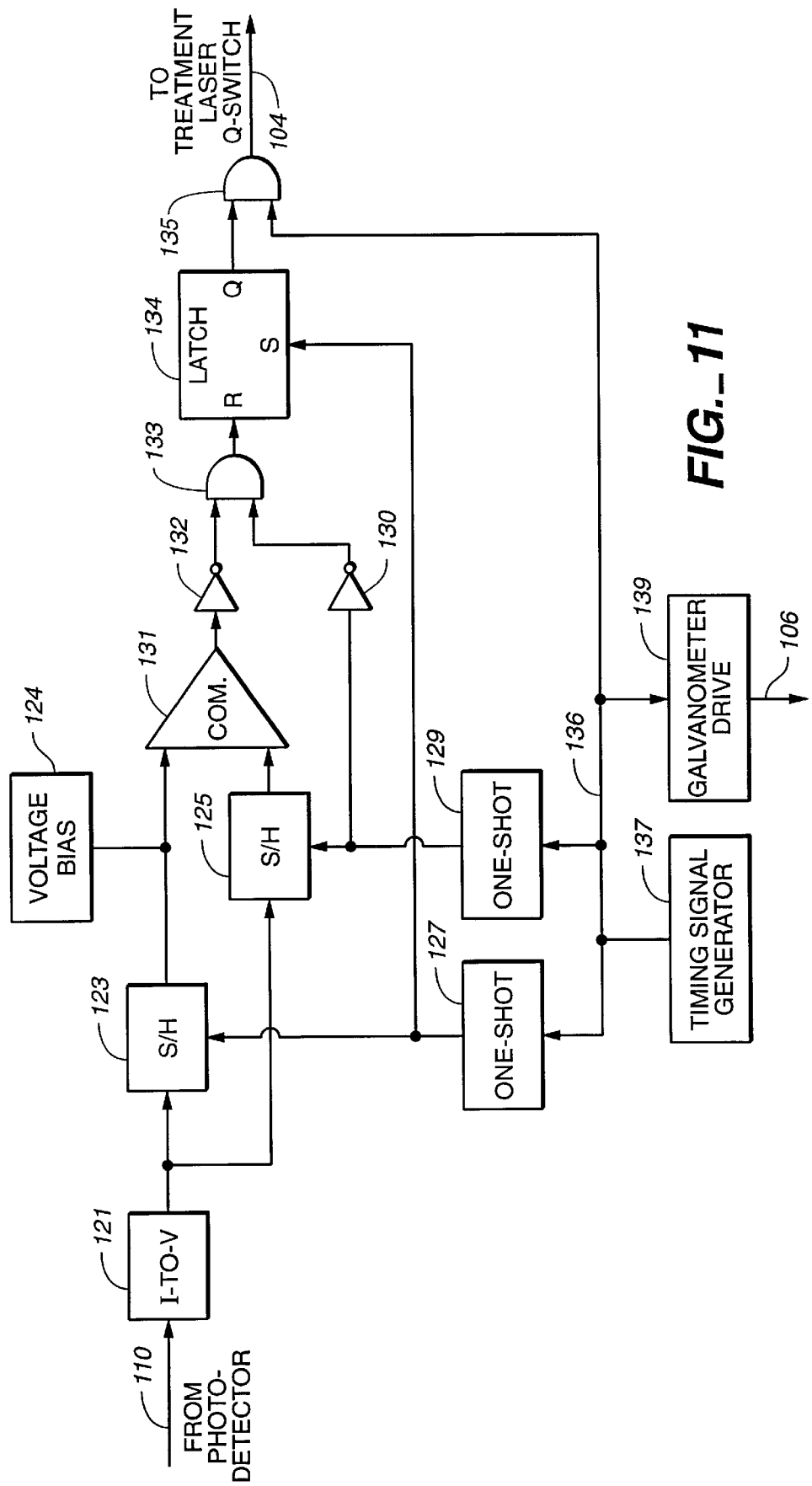
FIG._11

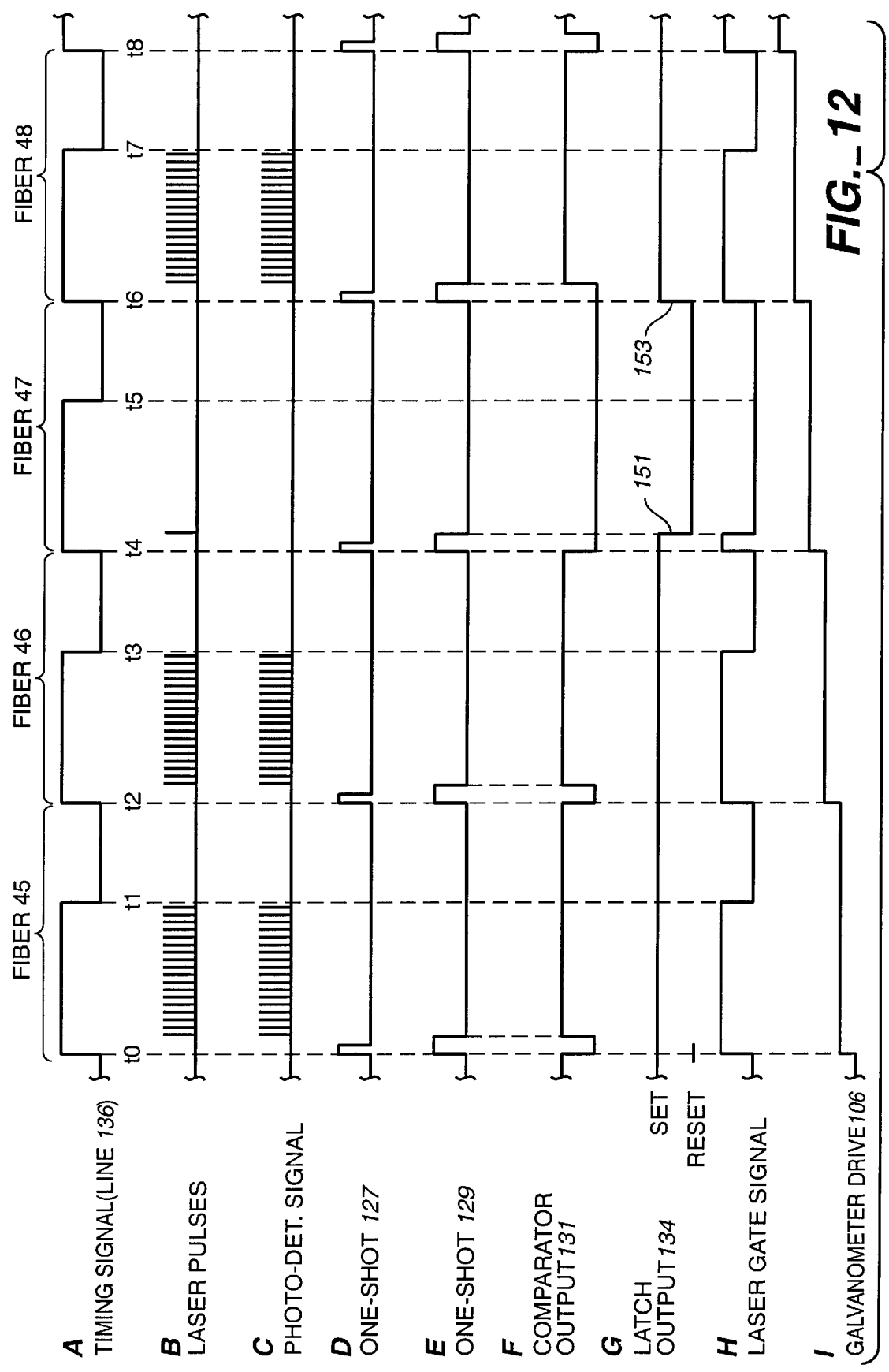
FIG._12

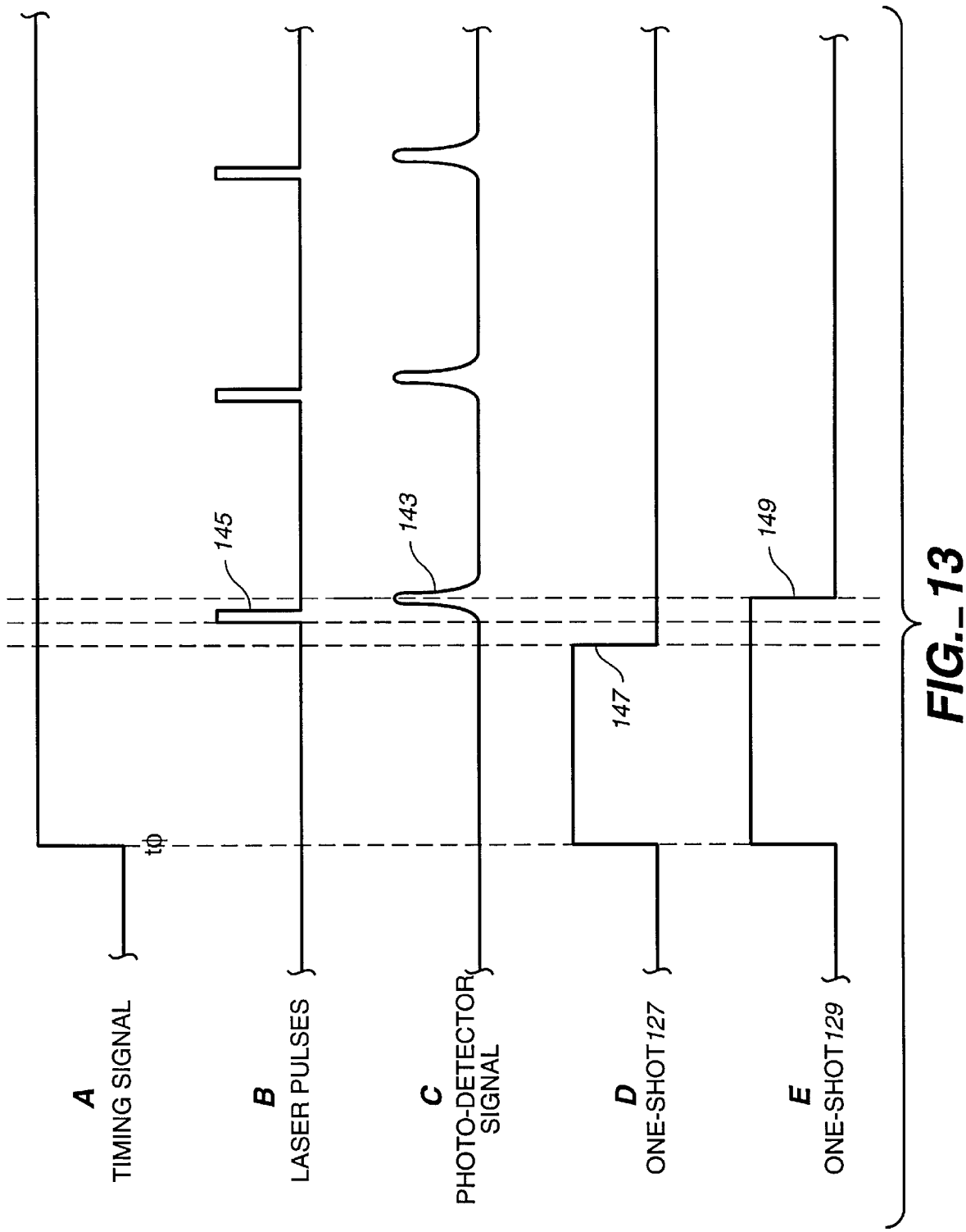
FIG._13

PHOTOACOUSTIC REMOVAL OF OCCLUSIONS FROM BLOOD VESSELS

CROSS-REFERENCE TO RELATED APPLICATIONS

This is a continuation of copending application Ser. No. 08/955,858, filed Oct. 21, 1997 now abandoned.

UNITED STATES GOVERNMENT RIGHTS

The United States Government has rights in this invention pursuant to Contract No. W-7405-ENG-48 between the United States Department of Energy and the University of California for the operation of Lawrence Livermore National Laboratory.

BACKGROUND OF THE INVENTION

This invention relates generally to the removal of a partial or total occlusion from a blood vessel by generating pressure waves within the vessel through optical fiber media, and, more specifically, to the removal of a blood clot from a vessel within the human brain. The term "clot" is used herein to refer to a thrombus, embolus or some other total occlusion of a vessel.

Medical procedures to open a partially or totally blocked blood vessel are available. Angioplasty has long been used to restore full blood flow in a coronary artery by mechanically deforming deposits on the arterial walls but has been less successful to open a totally occluded vessel. Laser techniques have been proposed to directly ablate obstructing material from arteries, such as plaque and certain types of clots, by inserting optical fibers into the artery to the point of the obstructing material but these techniques have enjoyed only limited success in practice. Various uses of ultrasonic energy to generate acoustic waves directed against plaque or a clot within an artery to mechanically break up the obstructing material have also been proposed but medical procedures utilizing these techniques have not enjoyed widespread acceptance. Photo acoustic techniques have been proposed for vasodilation and the break-up of plaque and clots in arteries, wherein one or more optical fibers are inserted into the vessel and pulses of radiation delivered to the vessel through the fibers generate a pressure or acoustic wave directed against the obstruction.

Major blood vessels within the brain are very small, generally not exceeding three millimeters in diameter and being much smaller than that in most places. Most cerebral blood vessels decrease in diameter along their lengths until becoming capillaries. Besides being small, the walls of cerebral vessels are more fragile than those of vessels in other parts of the body and are more loosely connected to surrounding tissue.

When a thrombus is formed or an embolus is lodged in a blood vessel of the brain, an ischemic stroke results. The resulting sudden cut off of the supply of fresh blood to cerebral vessels terminates the supply of oxygen to these vessels and to the brain tissue they supply. The seriousness of a stroke depends upon the amount of brain tissue involved and its location. Generally, the more serious strokes result when the larger cerebral vessels become blocked, since they supply more volume of tissue than the smaller vessels, but the blockage of vessels having a diameter of less than one millimeter, or even one-half of one millimeter or less, can be quite serious.

If a cerebral vessel of a stroke victim can be unblocked within about six hours after the blood flow is totally stopped, the effects of the stroke on the oxygen starved brain tissue are often largely reversed. If unblocked within this time, deterioration of the walls of the blocked vessel to the point of hemorrhaging is prevented. As a result, many have tried to develop techniques for removing clots from cerebral vessels within a few hours after a stroke has occurred.

One such technique is to position a catheter into the blocked vessel to mechanically remove the clot. But this is very difficult to do without causing further damage because the vessels are so small, contain very sharp turns, are weakly constrained and have fragile walls. Alternatively, a lytic drug is often applied intravenously, in an attempt to dissolve the clot without having to dislodge it mechanically. In an attempt to improve the rate of success of the lytic drug, it has been introduced directly into the blocked vessel through a catheter at the point of the blockage. But none of these techniques have enjoyed a high rate of success.

Therefore, it is a primary object of the present invention to provide techniques for reopening clotted blood vessels of the human brain with an increased rate of success.

It is another important object of the present invention to provide techniques to remove partial or total occlusions from other parts of the body.

It is a further object of the present invention to provide techniques for removing obstructions from the human body, particularly clots from cerebral blood vessels, without causing collateral damage to the vessel.

It is another object of the present invention to provide a practical instrument and system to perform these functions.

SUMMARY OF THE INVENTION

These and other objects are accomplished by the various aspects of the present invention, wherein, briefly and generally, a catheter containing multiple small diameter optical fibers terminating in a two-dimensional pattern is positioned adjacent the occlusion and pulses of radiation are directed along the optical fibers, one at a time in sequence, with the individual pulses having a duration and amount of energy sufficient to generate a shock wave and, from an expansion and collapse of a bubble, a pressure wave, both of which are directed against the obstruction in order to break it up and restore the flow of blood through the vessel. Clots within either arteries or veins are emulsified in this manner.

It has been found that the use of very small diameter optical fibers allows the desired shock and pressure waves to be generated with a relatively low amount of radiation pulse energy, thereby keeping the amount of heat input to the vessel at a low level. Proper thermal management according to the present invention reduces the likelihood of damaging the walls of the blood vessel adjacent the occlusion, which is especially important for the relatively thin walled vessels of the brain. Further, it is desirable that radiation pulses not being efficiently converted into the desired pressure waves be terminated in order to prevent inputting energy that heats the region without doing useful work. In addition to keeping the power input low, a liquid coolant may be introduced through the catheter to carry heat away from the region of the occlusion during the treatment.

Additional objects, features and advantages of the various aspects of the present invention will be better understood from the following description of its preferred embodiments, which description should be taken in conjunction with the accompanying drawings.

BRIEF DESCRIPTION OF THE DRAWINGS

FIG. 1 illustrates an application of the present invention to remove a clot from a blood vessel in the brain, by use of a multi-optical fiber delivery system;

FIG. 2 shows a catheter of the present invention positioned in a blood vessel to emulsify a clot;

FIG. 3 is a perspective view of the catheter and delivery system of FIGS. 1 and 2;

FIG. 4 is a cross-sectional view of an end of an optical fiber used in the catheter of FIG. 3;

FIG. 5 show curves of the spectral radiation absorption by a blood vessel wall and a thrombus;

FIG. 6 schematically illustrates the exposure of the clot by radiation from the multiple optical fibers terminating in the end the catheter of FIG. 3;

FIGS. 7A–E schematically illustrate in time sequence the formation of shock and pressure waves by one of the optical fibers of the catheter of FIG. 3;

FIG. 8 includes a family of curves showing the amount of radiation pulse energy required to generate bubbles of various sizes for various sized optical fibers of the catheter of FIG. 3;

FIG. 9 is a three-dimensional graph that provides a comparison of a preferred range of parameters used in the present invention to a typical set of parameters used in the prior art;

FIG. 10 is an electro-optical diagram of the instrument shown in FIG. 1;

FIG. 11 is an electronic circuit block diagram of the system control of the instrument system of FIG. 10;

FIGS. 12A–I form a timing diagram showing various signals of the system control circuit of FIG. 11; and FIGS. 13A–E show a portion of the timing diagram of FIG. 12 with an expanded scale.

DESCRIPTION OF THE PREFERRED EMBODIMENTS

The present invention may, in general, be applied to the removal of material forming a partial or total occlusion of any human vessel but is particularly directed to opening a blood vessel that is totally or substantially blocked to the flow of blood. More specifically, the preferred embodiment of the present invention is directed to the removal of a clot from a blood vessel in the brain that has caused an ischemic stroke. If the flow of blood is restored in the vessel within a few hours of the onset of the stroke, permanent damage to the blocked vessels is avoided.

Before applying the techniques of the present invention to a patient with symptoms of a stroke, a physician first determines whether the stroke has been caused by a hemorrhage or a blockage of a cerebral vessel. This is usually determined by use of a standard computed tomography (CT) x-ray test. If it is determined by the CT test that the stroke has been caused by a blocked cerebral vessel, the blockage is located by use of a standard angiography test. This test may also be used to determine whether the blockage is a clot. This test is performed by injecting an x-ray contrast liquid into the vessels of at least that portion of the brain whose diminished function is believed to be responsible for the stroke, while taking x-rays of the brain. If a blockage exists in a vessel, a network of vessels beyond the blockage will not appear in the x-ray since the contrast liquid is prevented from flowing past the blockage. The vessel and position of the clot or other obstruction within the vessel is accurately determined in this manner.

A multiple optical fiber catheter having a lumen for carrying a cooling liquid is then inserted into that vessel with its end adjacent the blockage. One such insertion is illustrated in FIGS. 1 and 2. An elongated catheter 11 is inserted into a femoral artery 13 (FIG. 1) of a patient 15 and maneuvered through the appropriate arteries until an end 39 of the catheter (FIG. 2) is positioned within a blocked vessel 41, one of the cerebral vessels 17, adjacent a clot 43. The same insertion technique may be used here as presently used to introduce a catheter to inject a lytic drug directly into a clot in at attempt to dissolve it. A lytic drug may optionally be supplied through the lumen of the catheter 11 in order to dissolve at least some of the small particles that result from the emulsification of the clot by photo acoustic action. But use of the drug alone has not been found to be particularly effective.

The system of which the catheter 11 is a part is also shown generally in FIG. 1. A manifold 19 connects the lumen of the catheter 11 to a hose 21 having a connector 23 for removably connecting the hose 21 to a supply of liquid. The supply shown in FIG. 1 includes a pump 25 and reservoir 27. The primary purpose of delivering the liquid through the catheter is to remove heat from the region of the cerebral vessel that is being deposited by the emulsification process described below. This is part of the overall control of the heat flow in the region that has a purpose of avoiding thermal damage to the thin cerebral vessel walls. These small vessels are particularly susceptible to such damage if the photo acoustic process is not properly controlled. The flow of liquid into this region also helps in carrying away small particles of the clot that result from its emulsification, and keeps the ends of the optical fibers free of debris. The liquid may be isotonic saline or water, or some other biocompatible cooling agent of a type commonly used in medicine. Optionally, as mentioned above, a lytic drug can be included in the liquid to assist in dissolving these small particles. A lytic drug is more effective to dissolve the particles of the clot than in dissolving the clot itself since there is a greatly increased surface area to absorb the drug.

The manifold 19 also extends the optical fibers of the catheter 11 as a bundle 29 to a multi-fiber connector 31 that is removably connected to an instrument 33. This instrument contains the optics and electronics required to perform the medical procedure. Included on its face are various control switches or a keypad 35 and a display 37.

Referring to FIG. 3, the delivery system of FIG. 1 is shown by itself. This delivery system is replaceable, since it detaches from both the liquid pump 25 and instrument 33, and is optionally disposable after one use. Six optical fibers 45–50 terminating at one end in the connector 31 are shown to terminate at their other ends at the catheter end 39 by surrounding an opening of a lumen 51 that forms a fluid passage between the catheter end 39 and the hose 21. The optical fibers are attached to an inside surface of an outer flexible shell 53 of the catheter 11. Optionally, the lumen 51 is formed by a cylindrically shaped shell 55 on an inside of the optical fibers 45–50. The shell 55 may be omitted and the optical fibers need not be attached along the entire length of the catheter 11 in the same manner shown in FIG. 3 at its end 39. Although six optical fibers are shown for the purpose of this description, and will generally be the least number of fibers used, fewer or more fibers may be included. Generally, the ends of the optical fibers are spaced equidistant around the circumference of a circle at the end 39 of the catheter 11 around the lumen 51 but some other arrangement could be used.

Many of the cerebral vessels 17 (FIG. 1) in which it is desired to remove blockages are less than one millimeter in inside diameter (ID), and even as small as one-half of one millimeter, and seldom larger that three millimeters in inside diameter, as shown for the vessel 41 in FIG. 2. Therefore, an outside diameter (OD) of the catheter 11 (FIGS. 2 and 3), at least for a portion of its length adjacent its end 39 that passes through the cerebral vessels, must be small enough to maneuver the sharp turns of those very small vessels. The flexibility of at least that end length of the catheter must also be adequate to allow it to travel through the sharp turns of the small vessels, while at the same time being strong enough along its length to permit it to be pushed from outside of the patient. The distance that the end 39 of the catheter 11 travels from its insertion into the femoral artery 13 until reaching a clot within the brain is at least 50 or 75 centimeters for a child or small adult, averaging about 90 centimeters for an average sized adult. Therefore, the length of the catheter 11, between the manifold 19 and its end 39, is preferably at least 90 cm. for use with adults but can be as short as 50 or 75 cm. for use children or small adults. A usual length will generally be about 190 cm. in order to accommodate the additional use of manifolds for other purposes, such as to introduce a contrast fluid, when performing the procedures being described herein.

This combination of flexibility to bending and strength along its length can be accommodated in a catheter having an outside diameter (OD) of less than one-half a millimeter, a diameter within a range of 300 to 450 microns being preferred, with a 350 micron diameter being typical. A number of different designs for a long catheter of this diameter can be employed in order to provide the desired combination of flexibility and longitudinal strength. This includes the choices of materials and their thicknesses that are made, whether the lumen tube 55 is used, whether the optical fibers are attached to the catheter structure along the catheter other than at the end 39, and similar factors. Flexibility is improved when the optical fibers 45–50 are unattached along most of the length of the catheter within the lumen 51 but this can have the effect of restricting the amount of flow of liquid that is practical through the lumen and the longitudinal strength is not as great. The outside diameter and number of optical fibers used also affects these issues. A proper balance of these competing goals is achieved in a useful catheter assembly. The same considerations apply if a larger catheter is used, which could have up to a one millimeter outside diameter for cerebral or other vessels.

Each of the optical fibers 45–50 is chosen to be very small in diameter for reasons given below but this also contributes to the flexibility of the catheter 11. A cross-sectional view of a short length of an end of each of these fibers is shown in FIG. 4. A cylindrically shaped glass core 61 is surrounded by a glass cladding 63, which in turn is covered by a plastic sheath 65. Alternatively, one or both of the core and cladding may be plastic. In one specific embodiment, the diameter of the core 61 is 50 microns, with an overall outside diameter of 65 microns. Even smaller optical fibers are contemplated. A difference in the refractive indices of the materials of the core 61 and cladding 63, as is well known, defines the numeric aperture of the fiber. An angle a that defines the shape of a spreading cone 67 of radiation leaving the fiber end increases as this refractive index difference increases. This difference is chosen to be high for another reason, however. That is to increase the internal reflection within the core when the fiber is bent. This reduces radiation losses through the cladding when the fiber is bent through the sharp turns of the cerebral vessels in which it is positioned. For this purpose, materials are chosen for the core and cladding that have a difference in their refractive indices that is as high as practical. As the refractive index difference is increased, so is the difficulty and cost of making the optical fiber. Refractive index values that result in a numerical aperture in excess of 0.20 are practical, such as a numerical aperture of 0.22 or even 0.29.

With reference to FIG. 2, an introduction to how the catheter 11 is used to remove or provide an opening through the clot 43 is given. Radiation directed along each of the optical fibers 45–50 is converted into pressure waves within the vessel by a photo acoustic process. These pressure waves mechanically break the clot 43 apart by an emulsification process, with resulting small particles harmlessly traveling away from the site through the blood in the vessel 41. If the end 39 of the catheter 11 is spaced a distance away from the end surface of the clot 43, as is shown in FIG. 2, the repetitive pulses of radiation from the optical fibers are converted into pressure waves in liquid within the vessel 41, which is usually some combination of blood and cooling liquid along with small particles of the clot. The absorption of the radiation in this liquid depends upon the relative proportions of these three constituents. The cooling liquid is usually non-absorptive, and the blood and clot particles have similar spectral absorption characteristics. The higher the absorption, the stronger the pressure waves generated in the liquid for a given amplitude of radiation pulses.

Alternative to the radiation pulses being absorbed by the liquid, they may be absorbed by the clot 43 (FIG. 2) if the end 39 of the catheter 11 is positioned in the clot. The photo acoustic process then takes place within the clot. This will more often result when the clot 43 is a thrombus since a thrombus is generally soft. It is not difficult for the attending physician to urge the catheter a distance into the clot. In practice, the physician moves the catheter around in the vessel 41 during treatment, both across the face of the clot 43 and back and forth along the length of the vessel 41. The radiation pulses are then absorbed by the liquid some of the time and by the clot some of the time. As the clot is emulsified, the end 39 of the catheter 11 is moved by the physician against a disintegrating face of the clot until the end 39 has moved completely through it. This process does take some time since the clot 43 can have a substantial length. If the clot is a thrombus, it typically will be from one to four or more centimeters in length along the vessel 41.

Although it is desired that the clot 43 be highly absorptive of the radiation pulses, it is also desired that the wall of the blood vessel have a low absorption since it is difficult to prevent the radiation pulses being directed against the vessel wall, at least for an instant, as the catheter 11 is manipulated by the physician. The prevention of damage to the vessel wall is an important goal of the present invention. Fortunately, as shown in the curves of FIG. 5, a typical thrombus is much more absorptive than the vessel walls to electromagnetic radiation within the visible portion of the spectrum. A maximum difference in absorption, as can be seen from FIG. 5, occurs at a radiation wavelength of about 415 nanometers. In a practical instrument, however, a wavelength of about 532 nanometers (green) is used because lasers generating that wavelength are readily available, small in size, economical, trouble free and easy to use. A frequency doubled Q-switched laser with a neodymium ($Nd^{3+}$) doped host material provides the treatment pulses of radiation having a wavelength of about 532 nanometers,. depending upon the host material. YAG (yttrium aluminum garnet) or YLF (yttrium lithium fluoride) are examples of suitable hosts.

Referring to FIG. 6, the relative positions of an end of the clot 43 being treated and the end 39 of the catheter 11 are shown schematically. Dotted circles 45'–50' generally illustrate regions of the strongest portions of interaction of the shock and pressure waves that are generated by radiation pulses from respective optical fibers 45–50. In general, when operating within the parameter ranges described below, the individual regions 45'–50' have about twice the diameter of the cores of the respective optical fibers 45–50. It is useful if the regions 45'–50' substantially meet but the effects of any gaps in regions of emulsification of the clot 43 are overcome by the physician moving the catheter 11 around during the treatment. Such movement is necessary, in any event, since the catheter end 39 is smaller than the clot 43, and emulsification across the entire surface is desired. Indeed, the end 39 of the catheter 11 can be eccentrically shaped so that rotation of the catheter by the physician causes the end 39 to move across the surface of the clot 43.

Several of the specific techniques of the present invention have a purpose of minimizing the elevation of the temperature of the vessel wall in order to avoid damaging the wall. One such technique is to direct radiation pulses along only one of the multiple fibers at a time. Another is to limit the number of successive radiation pulses from a single fiber, before switching to another, in order to avoid creating a "hot spot" that heats the vessel wall by conduction or convection. A single pulse from each fiber in sequence minimizes any hot spots but is not as effective in emulsifying the clot. The best emulsifying action occurs when the shock and pressure waves repeatedly impinge upon a common area of the exposed clot end surface at a high rate. In addition to maintaining a beneficial turbulence initiated by a set of shock and pressure waves, an extended series of such waves results in more finely emulsifying larger particles that are initially broken away from the clot before they drift too far away from the clot along the vessel. The smaller the particles resulting from the emulsification, the less risk that a particle will lodge somewhere else to block the same or another vessel.

Yet another thermal management technique involves directing successive bursts of pulses along fibers that are removed from one another in order to spread out the heat that is generated. For example, pulses from the fiber 46 can follow those from the fiber 49, followed by pulses from the fiber 47, then from the fiber 50, and so on, generally in a star pattern. Whatever specific sequence is used, it is usually desirable to have one fiber in between two fibers that carry radiation pulses in successive periods of time. In general, with reference to FIG. 6, one of the fibers 45–50 chosen to deliver the radiation at any instant in time is that which illuminates the coolest of the respective regions 45'–50' across the clot 43. If two or more of the regions are about the same temperature, then the region to receive radiation is randomly selected from the two or more coolest regions. The relative temperature of each region is dependent upon the amount of time since it and adjacent regions have been exposed, because each region receives heat by conduction from its adjacent regions as well as by absorbing radiation incident upon it. A particular sequence of illumination of the fibers can be intuitively established or determined by mathematically modeling the heat absorption and transfer characteristics for the clot and/or liquid being illuminated, in order to minimize the temperature rise within the vessel.

Although such skipping techniques can be the best for thermal management, it is not always the best for efficient emulsification. Especially when each burst of pulses through one fiber is only a few, or even just one pulse, before moving to the next fiber, it can be more efficient to direct such bursts through adjacent fibers so that the turbulence created from one fiber is built upon by pulses from the adjacent fiber, rather that moving to a fiber so far away that a momentum of emulsification must be started all over again. This also operates to allow pulses from one fiber to more finely emulsify at least some of any larger particles earlier broken away from the clot by pulses from an adjacent fiber.

The ultimate goal is to remove the clot with the least amount of heat being generated. When one set of radiation pulses is not as efficiently emulsifying the clot as another set, it will take more pulses overall to remove the clot and thus deliver a greater amount of heat in the process. There is thus a balance that is desired to be achieved between the direct reduction of heat input to the region of the clot from a particular spatial pattern of exposure to radiation pulses and a reduction of the amount of heat generated when the radiation pulses are used more efficiently. It may even be of some advantage to direct radiation pulses out of two or more of the optical fibers at one time but this is not preferred. Whatever pulse sequence is implemented, it is controlled by the electro-optical system within the instrument 33.

Referring to FIGS. 7A–E, the effect believed to result from one radiation pulse being directed out of a single optical fiber core 71 against an exposed face of a clot 73 is explained. In this example, the radiation is absorbed by the liquid in front of the clot 73. The effects will be similar if the absorption is in the clot itself. In either case, radiation is absorbed according to an absorption coefficient of the material in which the radiation is directed, and this absorbed energy superheats water within the material. According to the present invention, each pulse contains a small amount of energy, in order to minimize the amount of heat generated in the region, but is delivered by a pulse having a very short duration. This increases the efficiency of the process, which is expressed in terms of the mass of the clot that is emulsified per unit of laser pulse energy delivered to the treatment site within the vessel.

Very shortly after the pulse has been delivered, as shown in FIG. 7A, a volume 75 of liquid immediately adjacent the end face of the fiber core 71 is superheated in a manner to generate a shock wave 77 that is directed against the clot surface 73. A shock wave is characterized by traveling at a speed greater than the speed of sound in the same medium. The shock wave does not contain a great deal of energy but is believed to be quite useful because of a very sharp change in pressure that occurs. In order to generate the shock wave, the radiation energy is deposited into the volume 75 in a time that is shorter than this volume can expand to relieve the increased pressure. Therefore, the radiation pulse is made to have a very short duration.

A short time later, as shown in FIG. 7B, a bubble 79 has started to form and a hydrodynamics effect takes place that includes a pressure wave and mass flow 81 being directed against the clot 73 by the bubble's growth. This flow travels at less than the speed of sound but contains considerably more energy than the shock wave. Depending upon the amount of radiation energy deposited, the bubble 79 is a "vapor" (higher energy) or a "cavitation" (lower energy) type of bubble. At a subsequent instant of time shown in FIG. 7C, the bubble 79 is of a maximum size, and then, as shown in FIG. 7D, begins to collapse as its interior pressure drops below the pressure of the surrounding material and the ambient pressure overcomes the kinetic energy of the hydrodynamics flow. This collapse causes a hydrodynamics effect including mass flow and a pressure wave 83 moving in a direction opposite to that of the initial hydrodynamics flow 81. If the bubble is symmetrically formed as shown in FIG. 7C, another shock wave also results from this collapse. This is a complex dynamic process where, in very simplified terms, the bubble expands from the energy input to the fluid, then cools and collapses after the energy input pulse is terminated.

It has been found that the efficiency of the emulsification process is improved when both of the shock wave and hydrodynamics effect are generated by individual radiation pulses but only one or the other of them may be satisfactory for some applications and/or circumstances. At a later time of FIG. 7E, equilibrium again exists but only after some of the clot surface 73 has been broken away in response to the shock wave(s), hydrodynamics flow and liquid turbulence created by the mechanical motion of the flow. This process is repeated by each of subsequent radiation pulses.

Preferred Process Parameters

In order to remove a clot without creating thermal effects that have a potential of damaging a vessel wall, certain ranges of relative parameters have been discovered to work best. As mentioned above, it is a goal to have an efficient process. This minimizes the amount of laser energy required, and thus the cost and complexity of the laser source used in the instrument, and also minimizes the amount of time required to remove a clot. Maximizing the efficiency is possibly most important in minimizing the heat imparted to the treatment site in the course of removing a given volume of the clot, thus reducing the chance for tissue damage, particularly to the thin blood vessel walls.

A first parameter of interest is the size of the individual optical fibers 45–50, which are preferably made to be the same. It has been found that efficiency is increased by using smaller fibers, contrary to what one might initially think. Optical fibers with a core diameter of 200 microns or less can be used but those with a core diameter of 100 microns or less are preferred. The fiber cores must be large enough, however, to withstand the destructive effects on the fiber of the shock wave and hydrodynamics flow being generated at its tip. Depending upon the other parameters, the smallest core diameter that is practical is about 20 microns. Another factor that affects the minimum size of the optical fiber is commercial availability and cost. Optical fibers with the 50 micron core diameter mentioned above are available, and 25 micron core fibers may soon be available at a reasonable cost.

It has been found, as illustrated by the family of curves of FIG. 8, that the size of the bubble generated, and thus the intensity of the pressure waves generated by its expansion and collapse, is controlled by more than the fiber size and can be made much bigger than the size of the fiber by use of appropriate levels of energy per pulse. In a specific example of a fiber with a 50 micron core diameter, a low energy of 100 micro-Joules per pulse generates a bubble having a maximum diameter (FIG. 7C) of 120 microns. This is read from the 50 micron curve of FIG. 8. It will also be noted from FIG. 8 that if it is desired to generate a certain bubble diameter, increasing the size of the optical fiber also requires increasing the amount of energy per pulse. Thus, the same amount of work can be performed by a bubble generated through a smaller fiber with a lower level of energy. The lower level of energy means that the heat deposited into the vessel in the region of the clot (treatment site) is also reduced, thus contributing to the goal of increased efficiency.

The amount of radiation energy delivered from the end of a single optical fiber by each of the individual pulses is chosen from the curve of FIG. 8 for the diameter of the core of the optical fiber being used. (Of course, other curves can be added for other than the 50, 100 and 200 micron core diameters shown.) A lower limit is that which will generate both the initial shock wave (FIG. 7A) and the bubble induced hydrodynamics flow (FIGS. 7B–D) since it has been found most efficient to use both in the emulsification process. This lower limit is about 10 micro-Joules for very small optical fibers and 50 micro-Joules for others, with 100 micro-Joules being usable with a 50 micron core diameter fiber, for example. In general, it is desired to provide as much energy as possible in each radiation pulse since it takes a substantial amount of base energy to raise the temperature of the material adjacent the optical fiber end to the boiling point of water and then further supply the heat of vaporization. Additional amounts of energy supplied above this base energy level are then more efficiently converted to useful work in emulsifying the clot by increasing the intensity of the shock wave and the size of the bubble. However, the amount of energy per pulse is kept below that which causes damage to the end of the optical fiber. For the small optical fibers described herein, the energy level is kept below about 250 micro-Joules per pulse per fiber.

The width of each radiation pulse is made relatively short in order to generate the initial shock wave. That is, the shock wave is generated as a result of a small volume of material at the end of the optical fiber (FIG. 7A) being heated very rapidly. This requires depositing the energy of the pulse in a very short period of time. A pulse width range of 1–100 nano-seconds has been found satisfactory. The "width" of a radiation pulse is defined for the purposes herein to be its duration at one-half its peak amplitude (known as "FWHM"—Full Width Half Max). In a specific implementation, a 20 nano-second pulse width is used with 100 micro-Joules of energy per pulse delivered through an optical fiber having a 50 micron core diameter.

A repetition rate of pulses directed against the same or adjacent regions of the clot should be high enough to keep the clot surface in a dynamic state and assure that any large particles are further emulsified before drifting away from the region. A pulse rate of about one kilo-Hertz or more is enough for this. The main consideration for an upper limit is to allow the bubble from one pulse to be fully formed and collapsed (FIGS. 7B–D) before the next pulse hits. A pulse rate of about 20 kilo-Hertz or less allows this to occur, although rates up to 50 kilo-Hertz may be possible in certain circumstances. A pulse repetition rate of 5 kilo-Hertz has been used with the other parameters of the specific implementation given above.

The average power delivered to the vessel and clot is maintained as low as possible in order to minimize thermal load of the treatment site within the vessel in a way that avoids damaging the vessel. A maximum average nominal operating power of 0.5 watt is desirably maintained over the time of the treatment, and preferably less than 300 milliwatts. The achievement of this low power level can require, in some cases, that the treatment be performed with a duty cycle of less than one, such as 0.6 or 0.8. That is, no radiation pulses are directed into the vessel during periodically occurring intervals such that the pulses are generated 60% or 80% of the time. The maximum power level that can be used without causing damage also depends upon whether a cooling liquid is discharged through the lumen 51, and if so, the rate of its flow. A liquid flow rate as little as 0.1 cubic centimeters per minute provides beneficial cooling results. A flow rate in excess of two cc./min. will seldom be necessary, and a rate in excess of five cc./min. is not contemplated. A rate of one cc./min. has been used with the other parameters given above for the specific implementation. The flow rate is chosen so as not to overburden the vascular system but yet provide sufficient cooling. The amount of heat generated, and thus the average power input to the blood vessel, is independent of the number of optical fibers that are used in the preferred case where pulses are directed through only one of the fibers at a time.

A comparison is illustrated in a three-dimensional graph of FIG. 9 of the combination of parameters used in the present invention with those typically used by others for a range of applications similar to what is being described herein but not specifically addressed to cerebral vessels. The three axes of the graph are energy per pulse per fiber, pulse duration and pulse repetition rate. The scaling of the graph is logarithmic. A point 87 indicates the combination of parameters given above for the specific implementation of the present invention. A point 89 shows those of a typical prior system, although specific different systems do have parameters that vary substantially from the values of the point 89. However, the present invention clearly utilizes much lower levels of energy per pulse (by a factor of approximately 500), much shorter pulses (by a factor of approximately 200) and much higher repetition rates (by a factor of approximately 100) than generally used before.

The Opto-Electronic Instrument

The structure and function of the instrument 33 (FIG. 1) is illustrated by FIG. 10. A treatment radiation source 91, preferably the Q-switched, frequency doubled Nd:YAG laser mentioned above, emits radiation pulses of a fixed frequency that is set to correspond to the desired pulse repetition rate discussed above. An input control signal 104 effectively turns the laser 91 on and off. The pulses are reflected from a dichroic mirror 93, then from another mirror 95 through an optical system 99 that focuses the laser output beam through an aperture of a mirror 101 onto the optical fiber connector 31. This beam is scanned in sequence across a line of the individual fibers 45–50 by a galvanometer 97 that controllably tilts its mirror 95 in response to a control signal from a controller 103.

The galvanometer 97 preferably holds the beam on a single optical fiber for a time to direct a burst of a given number of one to many pulses into that one fiber before moving the beam to another fiber. A drive signal 106 supplies the proper positioning voltage to the galvanometer, depending upon which optical fiber is to receive the output pulses of the laser 91. Movement from one fiber to another necessarily takes some time, during which none of the optical fibers receives a pulse. It will usually be preferable to reduce or eliminate this gap in delivering radiation pulses to the fibers. This can be done by substituting an acousto-optic modulator for the galvanometer 97 and mirror 95, to controllably scan the beam from the laser 91 across the ends of the optical fibers 45–50 held in the connector 31.

As mentioned above, part of the thermal management of the clot removal process preferably also includes monitoring whether bubbles are being generated by each of the optical fibers. If not, delivery of radiation pulses along that fiber is terminated, at least temporarily, since those pulses are likely delivering only heat to the affected blood vessel without performing any emulsification. This bubble monitoring and radiation pulse control is accomplished by the system shown in FIG. 10.

A second laser 105 is provided to monitor the existence of a bubble. It can be a simple continuous wave (cw) laser with an output within the visible portion of the radiation spectrum. Its output beam is chosen to have a sufficiently different wavelength from that of the treatment laser 91 to enable the two laser beams to be optically separated from each other. A helium-neon laser is appropriate, as is a simpler diode laser with an appropriate wavelength.

An output beam of the monitoring laser 105 is directed through the dichroic mirror 93 to strike the mirror 95 coaxially with the beam from the treatment laser 91. The monitoring beam is then scanned across the optical fibers 45–50 together and coaxially with the treatment beam. If the galvanometer 97 and mirror 95 are replaced with an acousto-optical modulator for scanning the treatment beam, another such modulator is used for the monitoring beam.

When a bubble is present at the end of an optical fiber receiving both of the treatment and monitoring beams, as shown in FIG. 7C, there is a reflection of the monitoring beam from an end surface of the fiber that has an interface with the inside of the bubble. When no bubble is present, as in FIG. 7E, there is a reflection of the monitoring beam from the fiber end surface which now interfaces with the liquid within the vessel or the clot itself. The amount of the intensity of the monitoring beam that is reflected is much different in each of these two cases because of the much different refractive indices of water vapor, in one case, and liquid or clot material, in the other case. The monitoring beam, which has been reflected from the fiber end at the bubble and then transmitted back through the fiber, emerges out of the end of the optical fiber, is reflected by the mirror 101 and focused by appropriate optics 107 onto a photodetector 109 which has an electrical output 110. This reflected monitoring beam is passed through a linear polarizer 111 to reject radiation reflected from the end of the optical fiber within the connector 31. A filter 113 is also placed in the path of the reflected monitoring beam in order to prevent reflected radiation from the treatment laser 91 from reaching the photodetector 109.

A block electronic circuit diagram for the system control 103 of FIG. 10 is given in FIG. 11, with several of its signals being given in the timing diagrams of FIGS. 12A–I and 13A–E. The signal 110 (FIGS. 12C and 13C) from the photodetector 109 is converted from a current to a voltage signal by a circuit 121. This voltage "bubble" signal is connected to two sample-and-hold circuits 123 and 125, the outputs of which are connected to two inputs of a comparator. 131. In order for the comparator 131 to operate properly, the output voltage of the sample-and-hold circuit 123 is shifted in voltage level by a constant voltage bias 124. This bias voltage is added to the reference measurement made prior to generation of the bubble. The circuits 123 and 125 store the value of the photodetector voltage signal at different times in response to the falling edges of respective one-shot multivibrator circuit 127 and 129 outputs (FIGS. 12D,E and 13D,E respectively). The one-shots 127 and 129 receive a timing signal (FIGS. 12A and 13A) in a circuit 136 from a timing signal generator 137.

An output of the comparator 131 (FIG. 12F) is inverted by an inverter 132, the output of which is connected to one input of an AND-gate 133. A second input to the AND-gate 133 is the output of the one-shot 129, after being inverted by an inverter 130. In practice, the inverted output usually may be obtained from the one-shot circuit 129 itself. An output of the AND-gate 133 goes high when the outputs of both the one-shot 129 and comparator 131 are low, an occurrence that takes place only when an expected reflection from a bubble is not being detected by the photodetector 109. This occurrence resets a latch 134 whose state (FIG. 12G) becomes one input to a two input AND-gate 135. The other input to the AND-gate 135 is the timing signal (FIGS. 12A and 13A) of the signal generator 137. The latch 134 is set by a rising edge of the output of the one-shot 127. The laser controlling signal 104 (FIG. 12H) is the output of the AND-gate 135. The drive signal 106 (FIG. 12I) that positions the mirror 95 of the galvanometer 97 is developed by a circuit 139 which is also synchronized with the timing signal (FIGS. 12A and 13A) from the signal generator 137.

The operation of the system shown in FIGS. 10 and 11 can be further understood with reference to its timing diagram of FIGS. 12A–I and 13A–E. One cycle of operation is indicated between times t0 and t2, when laser pulses are directed by the galvanometer 97 into the optical fiber 45. The next cycle occurs between times t2 and t4, when the pulses are directed into the fiber 46. Between times t4 and t6, in a next cycle, any laser pulses are directed to the fiber 47, and between times t6 and t8, laser pulses are directed to the fiber 48. Not shown are the operating cycles that follow to sequentially direct pulses along the remaining two optical fibers 49 and 50 of the example given. Once all of the fibers have received a train of pulses, the sequence is started over again and continues until the clot has been removed. Of course, the order in which the fibers carry the pulses may be something different, as previously discussed.

The timing signal of FIGS. 12A and 13A is clock driven, repetitively enabling (when high) and disabling (when low) the laser because it provides one of the inputs to the AND-gate 135. The specific form of timing signal illustrated imposes a duty cycle on the operation of the treatment laser 91 but this is not necessary in every application. By turning off the laser for a time (such as between times t1 and t2) after delivering a burst of pulses (such as between times to and t1) to individual ones of the optical fibers, the amount of heat delivered to the treatment site within the blocked blood vessel is reduced. This is another way to control the amount of average power that is delivered to the treatment site. In the example shown, pulses are delivered sixty percent of the time, so it is said that it is operating with a 60% duty cycle, but this is easily changed by changing the timing signal of FIGS. 12A and 13A.

In the example being given, a bubble is detected to be generated at the end of the fibers 45, 46 and 48 but is not so detected at the end of the fiber 47. That is, when a bubble is present, the photodetector signal 110 (FIGS. 12C and 13C) includes a pulse from light reflected from the monitoring laser 105 immediately after each pulse (FIGS. 12B and 13B) from the treatment laser 91. This is best shown in FIGS. 13B–C, wherein a reflected radiation pulse 143 occurs immediately after a treatment radiation pulse 145. The existence of the reflected pulse 143 is detected comparing values of the photodetector signal 110 just before and just after the treatment laser pulse.

The trailing edge 147 of the output of the one-shot 127 is caused to occur just prior to the treatment laser pulse 145. This is controlled by the length of the output pulse of the one-shot 127 and the rising edge of the timing signal of FIG. 13A. The rising edge of the timing signal of FIG. 13A causes both the one-shot pulse to begin and the Q-switch of the treatment laser 91 to be turned on. The Q-switch of the laser 91 is set for the laser 91 to emit its first pulse 145 at a set time after the rising edge of the timing signal of FIG. 13A. The result is to store in the sample-and-hold circuit 123 the value of the photodetector signal before the treatment pulse, as a reference. A trailing edge 149 of the output of the one-shot 129 is timed to occur immediately after the treatment laser pulse 145, when the pulse 143 occurs if a bubble has been generated by the just ended treatment pulse. The one-shot signal edge 149 causes the value of the photodetector output signal at that instant to be stored in the sample-and-hold circuit 125.

If there is a difference in the voltage levels stored in the sample-and-hold circuits 127 and 129, as adjusted by the voltage bias 124, which exceeds a preset amount, the output of the comparator 131 goes high, resulting in the latch 134 remaining in its set state. But if there is not at least this difference in the voltages stored in the sample-and-hold circuits 123 and 125, then the output of the comparator 131 goes low and this causes the latch 134 to be reset at the trailing edge of the pulse output of the one-shot 129. This combination of events is shown to occur at 151 in FIG. 12G when a bubble is not detected.

It will be noted that the existence or non-existence of the bubble is detected only after the first treatment laser pulse of each burst. If none is detected, as for the fiber 47 in this example, no further treatment pulses of that burst are allowed to occur. Further pulses are prevented by the latch 134 being reset at 151 (FIG. 12G) by the comparator 131. The treatment laser is then reenabled at 153 by the latch 134 being set from the rising edge of the output pulse of the one-shot 127. Also, the next time pulses are directed to the fiber 47, the same process occurs, namely the transmission of the first pulse of a burst. If a bubble is detected after that pulse, then the entire burst will occur. Thus, the existence of a bubble is examined each time a new optical fiber becomes addressed.

Of course, this is only one of many specific arrangements and timing that can be implemented. For example, the existence or non-existence of a bubble can be determined after each treatment laser pulse. Further, the lack of the detection of a bubble can be used to disable that fiber for more than one cycle, and perhaps for the entire treatment. In the case where only one or a very few pulses are contained in each burst, the detection of the absence of a bubble at the end of one fiber can be used to disable the system from sending treatment radiation pulses down that fiber for a certain number of cycles and then trying again.

Although the various aspects of the present invention have been described with respect to their preferred embodiments, it will be understood that the invention is entitled to protection within the full scope of the appended claims.

It is claimed:

1. A method of opening to the flow of blood a human blood vessel that is at least partially blocked by an occlusion, comprising:

providing optical fibers, each of the optical fibers having a core diameter of less than or equal to 200 microns and having an optical fiber end;

positioning within the vessel an array of the optical fiber ends; and directing a sequence of one or more pulses of radiation out of one or more of the optical fiber ends and subsequently directing a sequence of pulses of radiation out of one or more of the other of the optical fiber ends, the pulses individually having a duration of less than or equal to 100 nanoseconds and containing sufficient energy to generate at least one shock wave and at least one bubble in a volume immediately adjacent the optical fiber ends which together cause a portion of the occlusion to be disrupted.

2. The method according to claim 1, wherein said subsequently directing the sequence of pulses including directing the pulses in sequence along adjacent optical fibers.

3. The method according to claim 1, wherein said subsequently directing the sequence of pulses includes directing the pulses in sequence along optical fibers that are not adjacent to each other.

4. The method according to claim 1, wherein each of the optical fibers has a core diameter of 50 microns or less.

5. The method according to claim 1, further comprising advancing the array of the optical fiber ends through the occlusion as the occlusion is disrupted until a blockage to the flow of blood through the vessel is removed.

6. The method according to claim 1, further comprising providing a cooling agent to the vessel.

7. The method according to claim 6, wherein the cooling agent is provided at a flow rate of from about 0.1 cc/min to about 5 cc/min.

8. The method according to claim 6, wherein the cooling agent is provided at a flow rate of from about 0.1 cc/min to about 2 cc/min.

9. The method according to claim 1 or claim 6, wherein the energy is below that which causes damage to the optical fiber ends.

10. The method according to claim 1 or claim 6, wherein the energy is below that which causes damage to a wall of the vessel.

11. The method according to claim 1, wherein the radiation is sufficient for absorption in material within the volume.

12. The method according to claim 1, wherein the radiation is sufficient to avoid absorption by a wall of the vessel sufficient to damage the wall.

13. The method according to claim 1, wherein the radiation has a wavelength within a visible portion of an electromagnetic spectrum.

14. The method according to claim 13, wherein the radiation has a wavelength of about 415 nanometers.

15. The method according to claim 13, wherein the radiation has a wavelength of about 532 nanometers.

16. The method according to claim 1, further comprising providing a lytic drug to the vessel.

17. The method according to claim 1, wherein the vessel is a cerebral vessel.

18. The method according to claim 17, wherein said providing optical fibers comprises providing optical fibers via a catheter of a construction sufficient for said positioning of the array in the cerebral vessel.

19. The method according to claim 1, further comprising optically monitoring said method for a characteristic selected from a group consisting of an absence of the at least one bubble, a presence of the at least one bubble, a characteristic of the at least one bubble, and any combination thereof.

20. A method of opening to the flow of blood a human blood vessel that is at least partially blocked by an occlusion, comprising:

providing optical fibers, each of the optical fibers having a core diameter of less than or equal to 200 microns and having an optical fiber end;

positioning within the vessel an array of the optical fiber ends; and directing a sequence of one or more pulses out of one or more of the optical fiber ends and subsequently directing a sequence of pulses of radiation out of one or more of the other of the optical fiber ends, the pulses individually having a duration of less than or equal to 100 nanoseconds and containing energy of less than 250 microJoules, the energy being sufficient to generate at least one shock wave and at least one bubble in a volume immediately adjacent the optical fiber ends which together cause a portion of the occlusion to be disrupted.

* * * * *